United States Patent [19]

Hofer et al.

[11] 4,088,758
[45] May 9, 1978

[54] O-(1-PHENYL-2-CARBALKOXY-VINYL)-THIONOPHOSPHORIC (PHOSPHONIC) ACID ESTERS AND ESTER-AMIDES AND METHOD FOR COMBATTING INSECTS

[75] Inventors: Wolfgang Hofer; Fritz Maurer; Hans-Jochem Riebel; Rolf Schröder, all of Wuppertal; Paul Uhrhan, Cologne; Bernhard Homeyer, Leverkusen; Ingeborg Hammann, Cologne, all of Germany

[73] Assignee: Bayer Aktiengesellschaft, Leverkusen, Germany

[21] Appl. No.: 709,994

[22] Filed: Jul. 30, 1976

[30] Foreign Application Priority Data

Aug. 20, 1975 Germany .................. 2536977

[51] Int. Cl.² .................. A01N 9/36; C07F 9/40; C07F 9/165
[52] U.S. Cl. .................. 424/212; 260/941
[58] Field of Search .................. 260/941; 424/21 L

[56] References Cited

U.S. PATENT DOCUMENTS 3,035,079  5/1962  Beriger .................. 260/941
3,644,601  2/1972  Miller et al. .................. 260/941 X
3,784,589  1/1974  Large .................. 260/941

Primary Examiner—Anton H. Sutto

Attorney, Agent, or Firm—Burgess, Dinklage & Sprung

[57] ABSTRACT

O-(1-Phenyl-2-carbalkoxy-vinyl)-thionophosphoric (phosphonic) acid esters and ester-amides of the formula

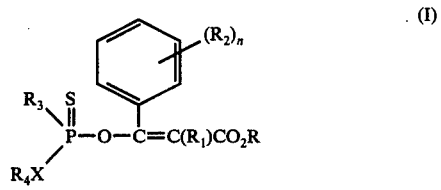

in which R and $R_4$ each independently is alkyl with 1 to 6 carbon atoms, $R_1$ is hydrogen or methyl, $R_2$ is alkyl, alkoxy or alkylthio each with 1 to 4 carbon atoms, cyano, halogen, or phenyl, $R_3$ is alkyl, alkylthio or alkylamino with 1 to 6 carbon atoms, or phenyl, X is oxygen or sulfur, and n is 0, 1, 2, 3, 4 or 5, which possess insecticidal and acaricidal properties.

9 Claims, No Drawings

O-(1-PHENYL-2-CARBALKOXY-VINYL)-THIONO-PHOSPHORIC (PHOSPHONIC) ACID ESTERS AND ESTER-AMIDES AND METHOD FOR COMBATTING INSECTS

The present invention relates to and has for its objects the provision of particular new O-(1-phenyl-2-carbalkoxy-vinyl)-thionophosphoric (phosphonic) acid esters and ester-amides which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from published Japanese patent application No. 18,736/62 and U.S. Pat. No. 3,102,842 that vinyl (thiono)phosphoric acid esters, for example O,O-dimethyl-O-[1-(2,4,5-trichlorophenyl)-2-chloro-vinyl]-phosphoric (Compound A) and -O-[1-(4-nitrophenyl)-2-carbethoxy-vinyl]-thiono-phosphoric acid ester (Compound B) possess an insecticidal and acaricidal action.

The present invention now provides, as new compounds, the vinyl(di- and tri)-thiophosphoric(phosphonic) acid esters and ester-amides of the general formula

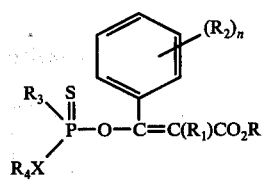

(I)

in which
R and $R_4$ each independently is alkyl with 1 to 6 carbon atoms,
$R_1$ is hydrogen or methyl,
$R_2$ is alkyl, alkoxy or alkylthio each with 1 to 4 carbon atoms, cyano, halogen, or phenyl,
$R_3$ is alkyl, alkylthio or alkylamino with 1 to 6 carbon atoms, or phenyl,
X is oxygen or sulfur, and
n is 0, 1, 2, 3, 4 or 5.

Preferably, R is alkyl with 1 to 3 carbon atoms, $R_4$ is alkyl with 1 to 5 carbon atoms, $R_2$ is cyano, fluorine, chlorine, bromine, iodine, phenyl, methyl, ethyl, methoxy, ethoxy, methylthio or ethylthio, $R_3$ is alkyl, alkylthio or monoalkylamino each with 1 to 5 carbon atoms per alkyl radical, or phenyl, X is oxygen and n is 0, 1, 2 or 3.

Surprisingly, the vinyl(di- and tri-)thiophosphoric(-phosphonic) acid esters and ester-amides according to the invention have a better insecticidal and acaricidal action than the corresponding vinyl(thiono)phosphoric acid esters of analogous structure, and of the same type of action, previously known from the state of the art. The products according to the present invention thus represent a genuine enrichment of the art.

The general formula (I) includes the corresponding cis- and trans-isomers of the structure (II) and (III) as well as the mixtures of these components:

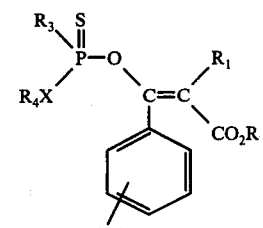

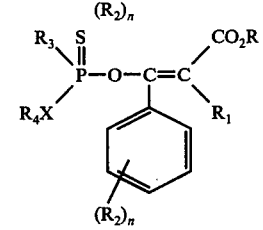

The present invention also provides a process for the preparation of a vinyl(di- or tri-)thiophosphoric(phosphonic) acid ester or ester-amide of the formula (I), in which a (di- or tri-)thiophosphoric(phosphonic) acid ester halide or ester-amide halide of the general formula

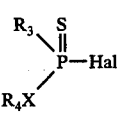

(IV)

in which
Hal represents halogen, preferably chlorine, is reacted with a benzoylacetic acid alkyl ester derivative of the formula (V), or its enol form (Va)

$$RO_2-C(R_1)CH-CO-\text{phenyl}(R_2)_n \quad (V)$$

$$RO_2C(R_1)C=C(OM)-\text{phenyl}(R_2)_n \quad (Va)$$

in which formula
M represents hydrogen or one equivalent of an alkali metal, alkaline earth metal or ammonium,
if appropriate in the presence of an acid acceptor and, if appropriate, in the presence of a solvent or diluent.

If, for example, O-ethyl-N-n-propylthionophosphoric acid ester-amide chloride and 2,4,5-trichlorobenzoylacetic acid n-propyl ester are used as starting materials, the course of the reaction can be represented by the following equation:

$$\begin{array}{c} C_2H_5O \\ \phantom{x} \\ n\text{-}C_3H_7\text{—NH} \end{array}\!\!\!\!\!\!\!\!\diagdown\!\!\!\overset{S}{\underset{\|}{P}}\!\!\!\diagup\!\!-Cl \; + \quad (IVa)$$

-continued

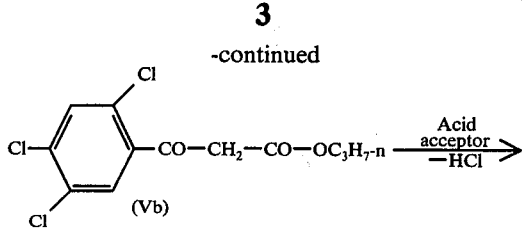

(Vb)

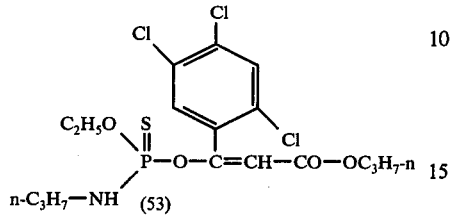

(53)

The (di- and tri-)thiophosphoric(phosphonic) acid ester halides and ester-amide halides (IV) required as starting materials are known and can be prepared in accordance with customary processes.

The following may be mentioned as individual examples: O,S-dimethyl-, O,S-diethyl-, O,S-di-n-propyl-, O,S-di-iso-propyl-, O,S,-di-n-butyl-, O,S-di-isobutyl-, O,S-di-tert.-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-isopropyl-, O-n-butyl-S-n-propyl- and O-sec.-butyl-S-ethyl-thiolthionophosphoric acid diester chloride; O-methyl-, O-ethyl-, O-n-propyl-, O-isopropyl-, O-n-butyl-, O-iso-butyl-, O-sec.-butyl-, O-tert.-butyl- and O-n-pentylmethane-, ethane-, n-propane, isopropane-, n-butane-, isobutane-, tert.-butane-, sec.-butane-, n-pentane- and benzene-thionophosphonic acid ester chloride; O-methyl-N-methyl-, O-ethyl-N-methyl-, O-n-propyl-N-methyl, O-isopropyl-N-methyl-, O-n-butyl-N-methyl-, O-sec.-butyl-N-methyl-, O-methyl-N-ethyl-, O-ethyl-N-ethyl-, O-n-propyl-N-ethyl-, O-isopropyl-N-ethyl-, O-n-butyl-N-ethyl-, O-sec.-butyl-N-ethyl-, O-methyl-N-n-propyl-, O-ethyl-N-n-propyl-, O-n-propyl-N-n-propyl-, O-n-propyl-N-n-butyl-, O-isopropyl-N-ethyl-, O-isopropyl-N-n-butyl- and O-tert.-butyl-N-ethyl-thionophosphoric acid ester-amide chloride; S-methyl-, S-ethyl-, S-n-propyl-, S-iso-propyl-, S-n-butyl-, S-sec.-butyl-, S-isobutyl-, S-tert.-butyl- and S-n-pentyl-methane, ethane-, n-propane-, isopropane-, n-butane-, isobutane-, sec.-butane-, tert.-butane- and benzene-thiolthionophosphonic acid ester chloride; and S-methyl-N-methyl-, S-ethyl-N-ethyl-, S-n-propyl-N-ethyl-, S-isopropyl-N-ethyl- and S-n-propyl-N-n-propyl-thiolthionophosphoric acid ester-amide chloride.

Benzoylacetic acid alkyl ester derivatives (V) and (Va) to be used as starting materials have also been described in the literature and can be prepared in accordance with the customary methods, e.g. German Published Specification DOS No. 2,343,974 and U.S. Pat. Nos. 2,407,942 and 2,367,632, whereas the α-benzoyl-propionic acid esters in question are producible from the sodium salts of the corresponding benzoylacetic acid alkyl esters by methylation, in accordance with processes known from the literature.

The following may be mentioned as individual examples: 4-cyano-, 4-phenyl-, 4-chloro-, 4-bromo-, 4-fluoro-, 4-iodo-, 4-ethylthio-, 4-methylthio-, 4-methoxy-, 4-ethoxy-, 4-methyl-, 4-ethyl-, 2-chloro-, 2-bromo-, 2-iodo-, 2-fluoro-, 2-methyl-, 2-ethyl-, 2-methoxy-, 2-ethoxy-, 2-methylthio-, 2-ethylthio-, 2-cyano-, 2,4-dichloro-, 2,4-dibromo-, 2,4-difluoro-, 2,4-diiodo-, 2,4-dimethyl-, 2,4-diethyl-, 2,5-dimethyl-, 2,5-diethyl-, 2,4,5-trichloro-, 2,4,5-tribromo- and 2,4,5-triiodo-benzoylacetic acid methyl ester, ethyl ester, n-propyl ester and isopropyl ester, as well as α-[4-cyano-, 4-phenyl-, 4-chloro-, 4-bromo-, 4-fluoro-, 4-iodo-, 4-ethylthio-, 4-methylthio-, 4-methoxy-, 4-ethoxy-, 4-methyl-, 4-ethyl-, 2-chloro-, 2-bromo-, 2-iodo-, 2-fluoro-, 2-methyl-, 2-ethyl-, 2-methoxy-, 2-ethoxy-, 2-methylthio-, 2-ethylthio-, 2-cyano-, 2,4-dichloro-, 2,4-dibromo-, 2,4-difluoro-, 2,4-diiodo, 2,4-dimethyl-, 2,4-diethyl-, 2,5-dimethyl-, 2,5-diethyl, 2,4,5-trichloro-, 2,4,5-tribromo- and 2,4,5-triiodo-benzoyl]-propionic acid methyl ester, ethyl ester, n-propyl ester and isopropyl ester.

The process for the preparation of the compounds according to the invention is preferably carried out in the presence of suitable solvents or diluents. Practically all inert organic solvents can be used for this purpose, especially aliphatic and aromatic optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C, preferably at 40° to 70° C.

In general, the reaction is allowed to take place under normal pressure.

To carry out the process, the thiophosphoric acid ester halide (IV) and the benzoylacetic acid ester derivative (V) or (Va) are preferably employed in equimolar amounts. An excess of one or other reactant produces no significant advantages. In most cases, the reaction is carried out in the presence of a solvent and in the presence of an acid acceptor. After completion of the reaction at the stated temperatures, an organic solvent, for example toluene, is added to the solution and the organic phase is worked up in the usual manner by washing, drying and distilling off the solvent.

The new compounds are obtained in the form of oils which in part cannot be distilled without decomposition but can be freed from the last volatile constituents by so-called "slight distillation," that is to say by prolonged heating under reduced pressure to moderately elevated temperatures, and can be purified in this way. They are characterized by the refractive index.

As already mentioned, the vinyl(di- and tri-)thiophosphoric(phosphonic) acid esters and ester-amides are distinguished by an excellent insecticidal and acaricidal activity. They are active against plant pests, pests harmful to health and pests of stored products and combine a low phytotoxicity and mammalian toxicity with a good action against both sucking and biting insects and against mites.

For this reason, the compounds according to the invention can be employed successfully as pesticides in plant protection as well as in the hygiene field and in the field of protection of stored products.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further cicadas, such as *Euscelis bilobatus* and *Nephotettix bipunctatus*.

In the case of the biting insects, above all there should be mentioned butterfly and moth caterpillars (*Lepidoptera*) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (*Coleoptera*), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, *Orthoptera*, for example the house cricket (*Gryllus domesticus*); termites such as the eastern subterranean termite (*Reticulitermes flavipes*) and *Hymenoptera* such as ants, for example the garden ant (*Lasius niger*).

The *Diptera* comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and blue bottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (*Acarina*) there are classed, in particular, the spider mites (*Tetranychidae*) such as the two-spotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 1

(*Myzus* test)

| Active compound | Active compound concentration in % | Degree of destruction in % after 1 day |
|---|---|---|
| 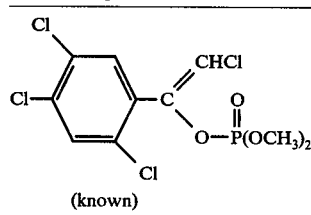<br>(known) | 0.1 | 0 |

Table 1-continued
(*Myzus* test)

| Active compound | Active compound concentration in % | Degree of destruction in % after 1 day |
|---|---|---|
| (23) 4-F-C₆H₄-C(=CH-CO-OCH₃)-O-P(=S)(OC₂H₅)(C₂H₅) | 0.1 | 100 |
| (31) 4-Cl-C₆H₄-C(=CH-CO-OCH₃)-O-P(=S)(OC₂H₅)(C₂H₅) | 0.1 | 99 |
| (32) 4-Cl-C₆H₄-C(=CH-CO-OCH₃)-O-P(=S)(OC₂H₅)(SC₃H₇-n) | 0.1 | 100 |
| (10) 4-Cl-C₆H₄-C(=C(CH₃)-CO-OCH₃)-O-P(=S)(OC₂H₅)(SC₃H₇-n) | 0.1 | 100 |
| (14) C₆H₅-C(=C(CH₃)-CO-OC₂H₅)-O-P(=S)(OC₂H₅)(SC₃H₇-n) | 0.1 | 100 |
| (5) C₆H₅-C(=CH-CO-OC₂H₅)-O-P(=S)(OC₂H₅)(C₂H₅) | 0.1 | 100 |
| (4) C₆H₅-C(=CH-CO-OC₂H₅)-O-P(=S)(OC₂H₅)(SC₃H₇-n) | 0.1 | 100 |
| (36) 4-Cl-C₆H₄-C(=CH-CO-OC₂H₅)-O-P(=S)(OC₂H₅)(C₂H₅) | 0.1 | 100 |
| (37) 4-Cl-C₆H₄-C(=CH-CO-OC₂H₅)-O-P(=S)(OC₂H₅)(SC₃H₇-n) | 0.1 | 100 |

Table 1-continued
(*Myzus* test)
| Active compound | Active compound concentration in % | Degree of destruction in % after 1 day |
|---|---|---|
| (26) 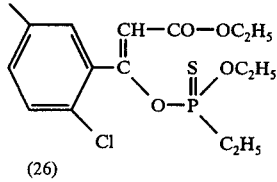 | 0.1 | 100 |
| (33) 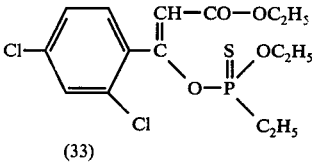 | 0.1 | 100 |
| (24) 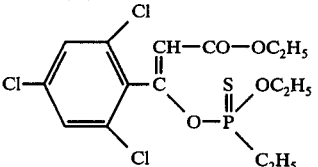 | 0.1 | 100 |
| (20) 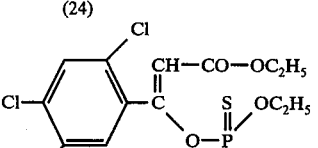 | 0.1 | 100 |
| (41) 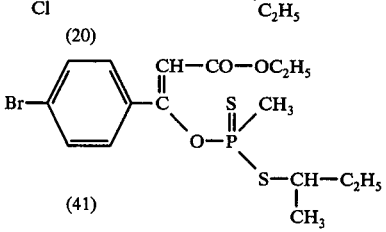 | 0.1 | 100 |
| (43) 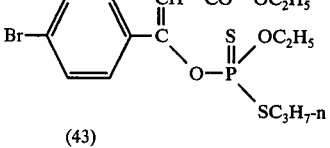 | 0.1 | 99 |
| (49) 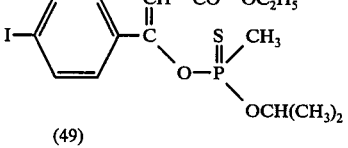 | 0.1 | 100 |
| (46) 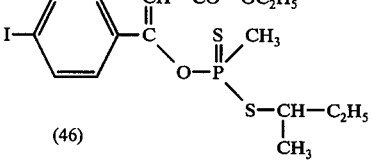 | 0.1 | 100 |
| (35) 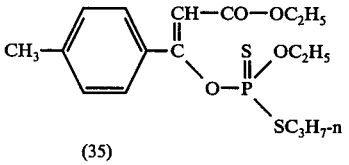 | 0.1 | 100 |

Table 1-continued
(Myzus test)

| Active compound | Active compound concentration in % | Degree of destruction in % after 1 day |
| --- | --- | --- |
| (21) 4-CH₃S-C₆H₄-C(=CH-CO-OC₂H₅)-O-P(=S)(OC₂H₅)(C₂H₅) | 0.1 | 100 |
| (6) 4-CH₃O-C₆H₄-C(=CH-CO-OC₂H₅)-O-P(=S)(CH₃)(OCH(CH₃)₂) | 0.1 | 99 |
| (2) 4-CH₃O-C₆H₄-C(=CH-CO-OC₂H₅)-O-P(=S)(OC₂H₅)(C₂H₅) | 0.1 | 100 |
| (38) 2-CH₃,5-CH₃-C₆H₃-C(=CH-CO-OC₂H₅)-O-P(=S)(CH₃)(S-CH(CH₃)-C₂H₅) | 0.1 | 100 |
| (40) 2-CH₃,5-CH₃-C₆H₃-C(=CH-CO-OC₂H₅)-O-P(=S)(OC₂H₅)(SC₃H₇-n) | 0.1 | 100 |
| (1) 2-CH₃,4-CH₃-C₆H₃-C(=CH-CO-OC₂H₅)-O-P(=S)(OC₂H₅)(CH₃) | 0.1 | 100 |
| (27) 2-CH₃,4-CH₃-C₆H₃-C(=CH-CO-OC₂H₅)-O-P(=S)(OCH(CH₃)₂)(CH₃) | 0.1 | 100 |
| (28) 2-CH₃,4-CH₃-C₆H₃-C(=CH-CO-OC₂H₅)-O-P(=S)(OCH₃)(C₂H₅) | 0.1 | 100 |
| (25) 2-CH₃,4-CH₃-C₆H₃-C(=CH-CO-OC₂H₅)-O-P(=S)(OC₂H₅)(C₂H₅) | 0.1 | 100 |

Table 1-continued

| Active compound | (*Myzus* test) Active compound concentration in % | Degree of destruction in % after 1 day |
|---|---|---|
| (29) Structure: 2,4-dimethylphenyl-C(=CH-CO-OC₂H₅)-O-P(=S)(OC₃H₇-n)(C₂H₅) | 0.1 | 100 |

EXAMPLE 2

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*) were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 2

| Active compound | (*Tetranychus* test/resistant) Active compound concentration in % | Degree of destruction in % after 2 days |
|---|---|---|
| (known) (A) 2,4,5-trichlorophenyl-C(=CHCl)-O-P(=O)(OCH₃)₂ | 0.1 | 0 |
| (known) (B) 4-nitrophenyl-C(=CH-CO-OC₂H₅)-O-P(=S)(OCH₃)₂ | 0.1 | 0 |
| (8) 4-chlorophenyl-C(=C(CH₃)-CO-OCH₃)-O-P(=S)(OC₂H₅)(C₂H₅) | 0.1 | 100 |
| (31) 4-chlorophenyl-C(=CH-CO-OCH₃)-O-P(=S)(OC₂H₅)(C₂H₅) | 0.1 | 99 |
| (10) 4-chlorophenyl-C(=C(CH₃)-CO-OCH₃)-O-P(=S)(OC₂H₅)(SC₃H₇-n) | 0.1 | 100 |

Table 2-continued
| Active compound | Active compound concentration in % | Degree of destruction in % after 2 days |
|---|---|---|
| 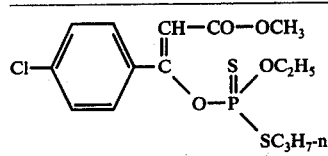 (32) | 0.1 | 100 |
| 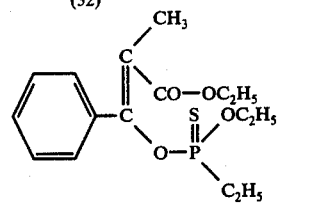 (11) | 0.1 | 98 |
| 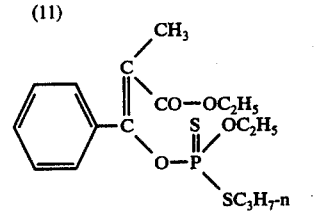 (14) | 0.1 | 100 |
| 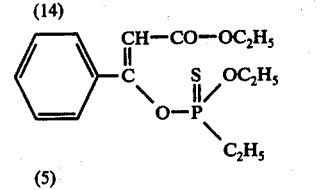 (5) | 0.1 | 100 |
| 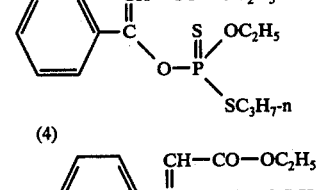 (4) | 0.1 | 100 |
| 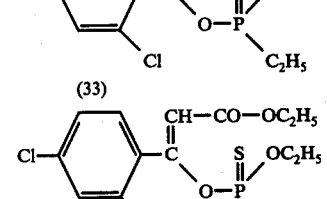 (33) | 0.1 | 100 |
| 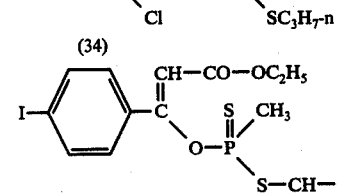 (34) | 0.1 | 99 |
| 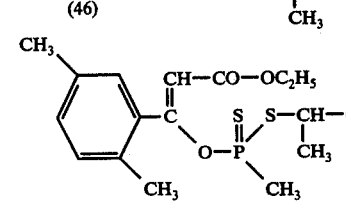 (46) | 0.1 | 100 |
| 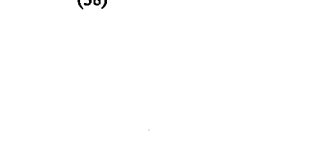 (38) | 0.1 | 100 |

Table 2-continued
(*Tetranychus* test/resistant)

| Active compound | Active compound concentration in % | Degree of destruction in % after 2 days |
|---|---|---|
| (28) Structure: CH$_3$-phenyl(CH$_3$)-C(=CH-CO-OC$_2$H$_5$)-O-P(=S)(OCH$_3$)(C$_2$H$_5$) | 0.1 | 100 |
| (1) Structure: CH$_3$-phenyl(CH$_3$)-C(=CH-CO-OC$_2$H$_5$)-O-P(=S)(OC$_2$H$_5$)(CH$_3$) | 0.1 | 100 |
| (25) Structure: CH$_3$-phenyl(CH$_3$)-C(=CH-CO-OC$_2$H$_5$)-O-P(=S)(OC$_2$H$_5$)(C$_2$H$_5$) | 0.1 | 95 |

EXAMPLE 3

Test insect: Phorbia antiqua grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is hereinafter quoted in ppm (=mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects have been killed and was 0% if exactly as many test insects are still alive as in the case of the untreated control.

The active compounds, amounts used and results can be seen from the table which follows:

Table 3
(*Phorbia antiqua* grubs in the soil)

| Active compound | Degree of destruction in % at an active compound concentration of 5 ppm |
|---|---|
| (known) (B) Structure: NO$_2$-phenyl-C(=CH-CO-OC$_2$H$_5$)-O-P(=S)(OCH$_3$)$_2$ | 0 |

Table 3-continued
(*Phorbia antiqua* grubs in the soil)

| Active compound | Degree of destruction in % at an active compound concentration of 5 ppm |
|---|---|
| (33) Structure: Cl,Cl-phenyl-C(=CH-CO-OC$_2$H$_5$)-O-P(=S)(OC$_2$H$_5$)(C$_2$H$_5$) | 100 |
| (36) Structure: Cl-phenyl-C(=CH-CO-OC$_2$H$_5$)-O-P(=S)(OC$_2$H$_5$)(C$_2$H$_5$) | 100 |
| (25) Structure: CH$_3$-phenyl(CH$_3$)-C(=CH-CO-OC$_2$H$_5$)-O-P(=S)(OC$_2$H$_5$)(C$_2$H$_5$) | 100 |
| (26) Structure: Cl-phenyl(Cl)-C(=CH-CO-OC$_2$H$_5$)-O-P(=S)(OC$_2$H$_5$)(C$_2$H$_5$) | 100 |

Table 3-continued
(*Phorbia antiqua* grubs in the soil)

| Active compound | Degree of destruction in % at an active compound concentration of 5 ppm |
|---|---|
| (28) 4-CH₃, 2-CH₃ phenyl, CH=C(CO-OC₂H₅)-O-P(=S)(OCH₃)(C₂H₅) | 100 |
| (1) 4-CH₃, 2-CH₃ phenyl, CH=C(CO-OC₂H₅)-O-P(=S)(OC₂H₅)(CH₃) | 100 |
| (5) phenyl, CH=C(CO-OC₂H₅)-O-P(=S)(OC₂H₅)(C₂H₅) | 100 |
| (11) phenyl, C(CH₃)=C(CO-OC₂H₅)-O-P(=S)(OC₂H₅)(C₂H₅) | 100 |
| (38) 3-CH₃ phenyl, CH=C(CO-OC₂H₅)-O-P(=S)(S-CH(CH₃)C₂H₅)(CH₃), 2-CH₃ | 100 |

EXAMPLE 4

Test insect: Tenebrio molitor larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is hereinafter quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the table which follows:

Table 4
(*Tenebrio molitor* larvae in the soil)

| Active compound | Degree of destruction in % at an active compound concentration of 5 ppm |
|---|---|
| (known) (B) 4-NO₂ phenyl, CH=C(CO-OC₂H₅)-O-P(=S)(OCH₃)₂ | 0 |
| (25) 4-CH₃, 2-CH₃ phenyl, CH=C(CO-OC₂H₅)-O-P(=S)(OC₂H₅)(C₂H₅) | 100 |
| (11) phenyl, C(CH₃)=C(CO-OC₂H₅)-O-P(=S)(OC₂H₅)(C₂H₅) | 100 |

The process of the present invention is illustrated in the following preparative Examples.

EXAMPLE 5 a. The benzoylacetic acid alkyl ester derivatives of the formula (VI) which are listed below and are required as starting materials were prepared in accordance with processes described in the literature, e.g. German Published Specification DOS No. 2,343,974.

$$\text{(R}_2\text{)}_n\text{-C}_6\text{H}_{5-n}\text{-CO-CH}_2\text{-CO-OR} \quad (VI)$$

| Intermediate | R | (R₂)ᵣ | Physical data (boiling point, °C/mm Hg; melting point, °C) | Yield (% of theory) |
|---|---|---|---|---|
| a | C₂H₅ | H | 115–120/1.5 | 87 |
| b | C₂H₅ | 4-OCH₃ | 170–178/1.0 | 85 |
| c | C₂H₅ | 4-CN | 140/0.1 | 84 |
| d | CH₃ | 4-Cl | 113/0.3 | 87 |
| e | C₂H₅ | 4-Cl | 125/0.1 | 86 |
| f | C₂H₅ | 4-C₂H₅ | 82 | 87 |
| g | CH₃ | 4-F | 115/0.05 | 52 |
| h | C₂H₅ | 4-I | 180/0.5 | 32 |
| i | C₂H₅ | 4-Br | 165/0.2 | 58 |
| j | C₂H₅ | 4-SCH₃ | 173/0.1 | 51 |
| k | C₂H₅ | 4-CH₃ | 148/1.0 | 76 |
| l | C₂H₅ | 2,5-Cl | 149/0.1 | 28 |
| m | C₂H₅ | 2,4-Cl | 155–165/0.3 | 30 |
| n | C₂H₅ | 2,5-CH₃ | 122–125/0.05 | 76 |
| o | C₂H₅ | 2,4-CH₃ | 130/0.05 | 74 |
| p | C₂H₅ | 2,4,5-Cl | 180–190/0.5 | 32 |
| q | C₂H₅ | 2,3,4-Cl | 160–170/0.1 | 10 |
| r | C₂H₅ | 2,4,6-Cl | 134/0.05 | 42.5 | b. The α-benzoylpropionic acid esters of the formula (VII) were obtained by methylation of the sodium salts of the corresponding benzoylacetic acid ester derivatives in accordance with processes known from the literature.

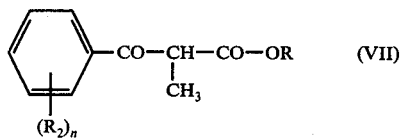

| Intermediate | R | (R$_2$)n | Physical data, (boiling point, °C/mm Hg; melting point, °C) | Yield (% of theory) |
|---|---|---|---|---|
| a | C$_2$H$_5$ | H | 114/0.1 | 83 |
| b | C$_2$H$_5$ | 4-Cl | 118–120/0.1 | 75 |
| c | CH$_3$ | 4-C$_6$H$_5$ | 195/0.05; 69 | 80 |
| d | C$_2$H$_5$ | 4-OCH$_3$ | 143–144/0.6 | 86 |
| e | C$_2$H$_5$ | 4-CN | 146/0.6 | 63 |
| f | C$_2$H$_5$ | 2,4-CH$_3$ | 125/0.05 | 52 |
| g | C$_2$H$_5$ | 2,5-CH$_3$ | 122/0.05 | 52 | c)

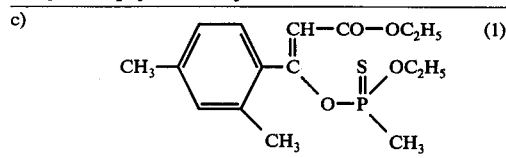

15.8 g (0.1 mole) of O-ethylmethanethionophosphonic acid ester chloride were added dropwise, without cooling, to a mixture of 22 g (0.1 mole) of 2,4-dimethylbenzoylacetic acid ethyl ester, 12.3 g (0.11 mole) of potassium tert.-butylate and 250 ml of acetonitrile. The reaction mixture was then warmed to 60° C and was stirred for 3 hours at this temperature. After cooling to room temperature, 400 ml of toluene were added. The batch was then extracted 3 times by shaking with 200 ml of water at a time, the toluene solution was dried over sodium sulfate and the solvent was distilled off under reduced pressure. The residue was subjected to slight distillation. 26 g (76% of theory), of O-ethyl-O-[1-(2,4-dimethylphenyl)-2-carbethoxyvinyl]-methanethionophosphonic acid ester were obtained in the form of a brown oil of refractive index n$_D^{20}$: 1.5403.

The following compounds of the general formula

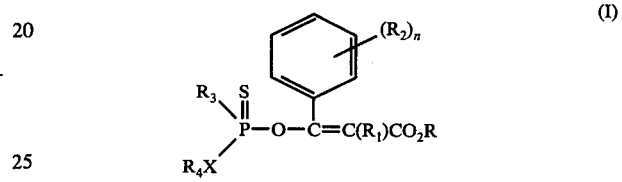

could be prepared analogously:

| Compound No. | R | R$_1$ | (R$_2$)$_n$ | R$_3$ | R$_4$ | X | Yield (% of theory) | Physical data (refractive index) |
|---|---|---|---|---|---|---|---|---|
| 2 | C$_2$H$_5$ | H | 4-OCH$_3$ | —C$_2$H$_5$ | —C$_2$H$_5$ | O | 84 | n$_D^{20}$: 1.5602 |
| 3 | C$_2$H$_5$ | H | H | —NH—C$_3$H$_7$-iso | —C$_2$H$_5$ | O | 10 | n$_D^{24}$: 1.5440 |
| 4 | C$_2$H$_5$ | H | H | —SC$_3$H$_7$-n | —C$_2$H$_5$ | O | 40 | n$_D^{24}$: 1.5536 |
| 5 | C$_2$H$_5$ | H | H | —C$_2$H$_5$ | —C$_2$H$_5$ | 0 | 58 | n$_D^{24}$: 1.5481 |
| 6 | C$_2$H$_5$ | H | 4-OCH$_3$ | —CH$_3$ | —C$_3$H$_7$-iso | O | 57 | n$_D^{23}$: 1.5470 |
| 7 | CH$_3$ | CH$_3$ | 4-CN | —C$_2$H$_5$ | —C$_2$H$_5$ | O | 53 | n$_D^{24}$: 1.5415 |
| 8 | CH$_3$ | CH$_3$ | 4-Cl | —C$_2$H$_5$ | —C$_2$H$_5$ | O | 72 | n$_D^{24}$: 1.5508 |
| 9 | CH$_3$ | CH$_3$ | 4-Cl | —C$_6$H$_5$ | —C$_2$H$_5$ | O | 51 | n$_D^{24}$: 1.5818 |
| 10 | CH$_3$ | CH$_3$ | 4-Cl | —SC$_3$H$_7$-n | —C$_2$H$_5$ | O | 72 | n$_D^{24}$: 1.5625 |
| 11 | C$_2$H$_5$ | CH$_3$ | H | —C$_2$H$_5$ | —C$_2$H$_5$ | O | 62 | n$_D^{23}$: 1.5315 |
| 12 | C$_2$H$_5$ | CH$_3$ | H | —NH—C$_3$H$_7$-iso | —C$_2$H$_5$ | O | 46 | n$_D^{23}$: 1.5272 |
| 13 | C$_2$H$_5$ | CH$_3$ | H | —C$_6$H$_5$ | —C$_2$H$_5$ | O | 51 | n$_D^{23}$: 1.5700 |
| 14 | C$_2$H$_5$ | CH$_3$ | H | —SC$_3$H$_7$-n | —C$_2$H$_5$ | O | 47 | n$_D^{24}$: 1.5492 |
| 15 | C$_2$H$_5$ | CH$_3$ | 4-OCH$_3$ | —C$_2$H$_5$ | —C$_2$H$_5$ | O | 97 | n$_D^{23}$: 1.5435 |
| 16 | C$_2$H$_5$ | CH$_3$ | 4-OCH$_3$ | —C$_6$H$_5$ | —C$_2$H$_5$ | O | 71 | n$_D^{23}$: 1.5690 |
| 17 | C$_2$H$_5$ | CH$_3$ | 4-OCH$_3$ | —CH$_3$ | —C$_3$H$_7$-iso | O | 59 | n$_D^{23}$: 1.5399 |
| 18 | CH$_3$ | CH$_3$ | 4-C$_6$H$_5$ | —CH$_3$ | —C$_3$H$_7$-iso | O | 45 | n$_D^{23}$: 1.5900 |
| 19 | C$_2$H$_5$ | H | 2,4,5-Cl | —C$_6$H$_5$ | —C$_2$H$_5$ | O | 53 | n$_D^{24}$: 1.5829 |
| 20 | C$_2$H$_5$ | H | 2,4,5-Cl | —C$_2$H$_5$ | —C$_2$H$_5$ | O | 44 | n$_D^{24}$: 1.5594 |
| 21 | C$_2$H$_5$ | H | 4-SCH$_3$ | —C$_2$H$_5$ | —C$_2$H$_5$ | O | 70 | n$_D^{24}$: 1.5663 |
| 22 | C$_2$H$_5$ | H | 4-SCH$_3$ | —C$_6$H$_5$ | —C$_2$H$_5$ | O | 42 | n$_D^{24}$: 1.6078 |
| 23 | CH$_3$ | H | 4-F | —C$_2$H$_5$ | —C$_2$H$_5$ | O | 60 | n$_D^{24}$: 1.5327 |
| 24 | C$_2$H$_5$ | H | 2,4,6-Cl | —C$_2$H$_5$ | —C$_2$H$_5$ | O | 83 | n$_D^{25}$: 1.5544 |

-continued

| Compound No. | R | $R_1$ | $(R_2)_n$ | $R_3$ | $R_4$ | X | Yield (% of theory) | Physical data (refractive index) |
|---|---|---|---|---|---|---|---|---|
| 25 | $C_2H_5$ | H | 2,4-$CH_3$ | —$C_2H_5$ | —$C_2H_5$ | O | 87 | $n_D^{25}$: 1.5305 |
| 26 | $C_2H_5$ | H | 2,5-Cl | —$C_2H_5$ | —$C_2H_5$ | O | 74 | $n_D^{23}$: 1.5460 |
| 27 | $C_2H_5$ | H | 2,4-$CH_3$ | —$CH_3$ | —$C_3H_7$-iso | O | 79 | $n_D^{20}$: 1.5357 |
| 28 | $C_2H_5$ | H | 2,4-$CH_3$ | —$C_2H_5$ | —$CH_3$ | O | 73 | $n_D^{20}$: 1.5455 |
| 29 | $C_2H_5$ | H | 2,4-$CH_3$ | —$C_2H_5$ | —$C_3H_7$-n | O | 84 | $n_D^{20}$: 1.5400 |
| 30 | $C_2H_5$ | H | 2,4-$CH_3$ | —$C_2H_5$ | 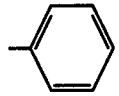 | O | 69 | $n_D^{20}$: 1.5702 |
| 31 | $CH_3$ | H | 4-Cl | —$C_2H_5$ | —$C_2H_5$ | O | 84 | $n_D^{22}$: 1.5529 |
| 32 | $CH_3$ | H | 4-Cl | —$SC_3H_7$-n | —$C_2H_5$ | O | 59 | $n_D^{22}$: 1.5533 |
| 33 | $C_2H_5$ | H | 2,4-Cl | —$C_2H_5$ | —$C_2H_5$ | O | 73 | $n_D^{26}$: 1.5426 |
| 34 | $C_2H_5$ | H | 2,4-Cl | —$SC_3H_7$-n | —$C_2H_5$ | O | 61 | $n_D^{26}$: 1.5560 |
| 35 | $C_2H_5$ | H | 4-$CH_3$ | —$SC_3H_7$-n | —$C_2H_5$ | O | 42 | $n_D^{22}$: 1.5631 |
| 36 | $C_2H_5$ | H | 4-Cl | —$C_2H_5$ | —$C_2H_5$ | O | 84 | $n_D^{23}$: 1.5513 |
| 37 | $C_2H_5$ | H | 4-Cl | —$SC_3H_7$-n | —$C_2H_5$ | O | 57 | $n_D^{25}$: 1.5518 |
| 38 | $C_2H_5$ | H | 2,5-$CH_3$ | —$CH_3$ | —$C_4H_9$-sec. | S | 84 | $n_D^{25}$: 1.5530 |
| 39 | $C_2H_5$ | H | 2,5-$CH_3$ | —$C_2H_5$ | —$C_2H_5$ | O | 71 | $n_D^{23}$: 1.5481 |
| 40 | $C_2H_5$ | H | 2,5-$CH_3$ | —$SC_3H_7$-n | —$C_2H_5$ | O | 86 | $n_D^{23}$: 1.5486 |
| 41 | $C_2H_5$ | H | 4-Br | —$CH_3$ | —$C_4H_9$-sec. | S | 75 | $n_D^{22}$: 1.5513 |
| 42 | $C_2H_5$ | H | 4-Br | —$C_2H_5$ | —$C_2H_5$ | O | 88 | $n_D^{24}$: 1.5483 |
| 43 | $C_2H_5$ | H | 4-Br | —$SC_3H_7$-n | —$C_2H_5$ | O | 88 | $n_D^{21}$: 1.5545 |
| 44 | $C_2H_5$ | H | 2,5-$CH_3$ | —$C_2H_5$ | 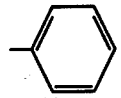 | O | 74 | $n_D^{25}$: 1.5561 |
| 45 | $C_2H_5$ | H | 2,5-$CH_3$ | —$CH_3$ | —$C_2H_5$ | O | 89 | $n_D^{21}$: 1.5521 |
| 46 | $C_2H_5$ | H | 4-I | —$CH_3$ | —$C_4H_9$-sec. | S | 98 | $n_D^{25}$: 1.5362 |
| 47 | $C_2H_5$ | H | 2,5-$CH_3$ | —$C_4H_9$-sec. | —$C_2H_5$ | O | 98 | $n_D^{24}$: 1.5461 |
| 48 | $C_2H_5$ | H | 4-Br | —$CH_3$ | —$C_3H_7$-iso | O | 89 | $n_D^{24}$: 1.5510 |
| 49 | $C_2H_5$ | H | 4-I | —$CH_3$ | —$C_3H_7$-iso | O | 94 | $n_D^{20}$: 1.5770 |
| 50 | $C_2H_5$ | H | 4-I | —$C_4H_9$-sec. | —$C_2H_5$ | O | 90 | $n_D^{21}$: 1.5602 |
| 51 | $C_2H_5$ | H | 4-I | | —$C_2H_5$ | O | 74 | $n_D^{21}$: 1.6141 |
| 52 | $C_2H_5$ | H | 4-Br | 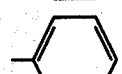 | —$C_2H_5$ | O | 99 | $n_D^{21}$: 1.5880 |

Other compounds which can be similarly prepared include:

| Compound No. | R | $R_1$ | $(R_2)_n$ | $R_3$ | $R_4$ | X |
|---|---|---|---|---|---|---|
| 53 | $C_3H_7$-n | H | 2,4,5-Cl | —NH—$C_3H_7$-n | —$C_2H_5$ | O |
| 54 | $C_3H_7$-iso | H | 4-$SC_2H_5$ | —$SCH_3$ | —$CH_3$ | S |
| 55 | $C_5H_{11}$-n | H | 4-$C_2H_5$ | —$N(CH_3)_2$ | —$C_5H_{11}$-n | O |
| 56 | $CH_3$ | H | 4-$OC_2H_5$ | —$NHCH_3$ | —$C_2H_5$ | O |
| 57 | $C_2H_5$ | H | 2-Cl,4-$CH_3$ | —$C_2H_5$ | —$C_2H_5$ | O | and the like.

It will be appreciated that the instant specification and examples are set forth by way of illustration and not limitation, and that various modifications and changes may be made without departing from the spirit and scope of the present invention.

What is claimed is:

1. An O-alkyl-O-(1-phenyl-2-carbalkoxyvinyl)-thionophosphoric(phosphonic) acid ester or esteramide of the formula

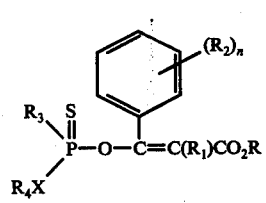

(I)

in which

R is alkyl with 1 to 3 carbon atoms,
$R_1$ is hydrogen or methyl,
$R_2$ is methyl, ethyl, methoxy, ethoxy, methylthio, ethylthio, chlorine, bromine, iodine, cyano or phenyl,
$R_3$ is alkyl, alkylthio or alkylamino with 1 to 5 carbon atoms, or phenyl,
$R_4$ is alkyl with 1 to 5 carbon atoms, and
$n$ is 0, 1, 2 or 3.

2. The compound according to claim 1, wherein such compound is O-ethyl-O-(1-phenyl-2-carbethoxyvinyl)-ethanethionophosphonic acid ester of the formula

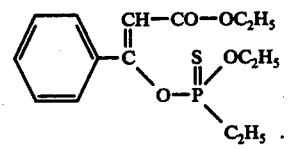

3. The compound according to claim 1, wherein such compound is O-ethyl-O-(1-phenyl-2-methyl-2-carbethoxyvinyl)-ethanethionophophonic acid ester of the formula

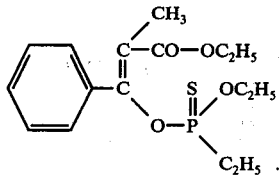

4. The compound according to claim 1, wherein such compound is O-methyl-O-[1-(2,4-dimethylphenyl)-2-carbethoxyvinyl]-ethanethionophosphonic acid ester of the formula

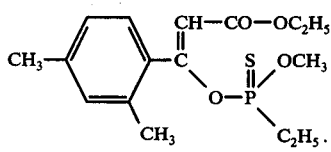

5. The compound according to claim 1, wherein such compound is O-ethyl-O-[1-(2,4-dichlorophenyl)-2-carbethoxyvinyl]-ethanethionophosphonic acid ester of the formula

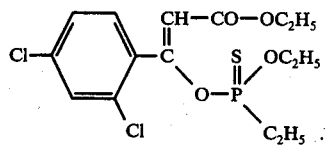

6. The compound according to claim 1, wherein such compound is O-ethyl-O-[1-(4-chlorophenyl)-2-carbethoxyvinyl]-ethanethionophosphonic acid ester of the formula

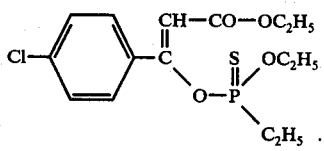

7. An insecticidal or acaricidal composition containing as active ingredient an insecticidally or acaricidally effective amount of a compound according to claim 1 in admixture with a diluent.

8. A method of combating insects or acarids which comprises applying to the insects or acarids or to a habitat thereof an insecticidally or acaricidally effective amount of a compound according to claim 1.

9. The method according to claim 8 in which said compound is

O-ethyl-O-(1-phenyl-2-carbethoxyvinyl)-ethanethionophosphonic acid ester,

O-ethyl-O-(1-phenyl-2-methyl-2-carbethoxyvinyl)ethanethionophosphonic acid ester, O-methyl-O-[1-(2,4-dimethylphenyl)-2-carbethoxyvinyl]-ethanethionophosphonic acid ester, O-ethyl-O-[1-(2,4-dichlorophenyl)-1-carbethoxyvinyl]-ethanethionophosphonic acid ester, or O-ethyl-O-[1-(4-chlorophenyl)-2-carbethoxyvinyl]-ethanethionophosphonic acid ester.

* * * * *

UNITED STATES PATENT AND TRADEMARK OFFICE
CERTIFICATE OF CORRECTION

PATENT NO. : 4,088,758
DATED : May 9, 1978
INVENTOR(S) : Wolfgang Hofer et al

It is certified that error appears in the above-identified patent and that said Letters Patent are hereby corrected as shown below:

Column 25, line 58, cancel "esteramide" and substitute therefor -- ester-amide-- .

Column 25, line 67, cancel "$R_4X$" and substitute therefor -- $R_4O$ -- .

Signed and Sealed this

Twenty-eighth Day of November 1978

[SEAL]

Attest:

RUTH C. MASON
Attesting Officer

DONALD W. BANNER
Commissioner of Patents and Trademarks